United States Patent [19]

Wasserman et al.

[11] 4,178,286

[45] Dec. 11, 1979

[54] β-LACTAMS, THEIR PRODUCTION, INTERMEDIATES THERETO AND DERIVATIVES THEREOF

[75] Inventors: Harry H. Wasserman; Bruce H. Lipshutz, both of New Haven, Conn.

[73] Assignee: Research Corporation, New York, N.Y.

[21] Appl. No.: 736,343

[22] Filed: Oct. 28, 1976

[51] Int. Cl.$^2$ .................... C07D 205/08; C07D 405/06
[52] U.S. Cl. .......................... 260/239 A; 260/239.3 R; 260/326.45; 260/326.13 B; 260/340.7; 260/340.9 R; 546/243; 549/49
[58] Field of Search .............. 260/239 A, 340.7, 340.9

[56] References Cited

PUBLICATIONS

Trost et al., J. Amer. Chem. Soc. 97, 3528–3530 (1975).
Yanulla et al., Tet. Letters 1968, 1725–1787.

*Primary Examiner*—Mark L. Berch
*Attorney, Agent, or Firm*—Haight & Huard

[57] ABSTRACT

γ-lactones are converted into both known and new azetidine carboxylic acids which can be transformed readily to the corresponding β-lactams by oxidative decarboxylation. The β-lactams and substitution products thereof are useful intermediates in the synthesis of biologically active lactams such as nocardicin.

7 Claims, No Drawings

β-LACTAMS, THEIR PRODUCTION, INTERMEDIATES THERETO AND DERIVATIVES THEREOF

BACKGROUND OF THE INVENTION

This invention was supported by grants GM-07874 and GM-13854 from the National Institutes of Health.

This invention relates to a process for the preparation of azetidine carboxylic acids and their conversion into the corresponding β-lactams, to further intermediates useful in the synthesis of biologically active β-lactams, and to methods for the synthesis thereof.

β-lactams have received increasing study as an essentail component in several families of compounds having useful biological, especially antibacterial, activity, e.g., the β-lactam-thiazolidine ring (penam) system common to all penicillins and the β-lactam-dihydrothiazine (cepham) nucleus common to the cephalosporins, and increasingly in monocyclic β-lactams which have been recently described. For example, Hashimoto et al, in JACS98(10):3023(May 12, 1976), have described the structure of nocardicin, a monocyclic β-lactam having antibacterial activity. A number of additional monocyclic β-lactams, many of which are structurally similar to the bicyclic penicillin and cephalosporins, have been described in Belgium Pat. No. 830,934 and by Bose et al in J.Med.Chem.17(4):541(1974).

At present, most monocyclic β-lactams are synthesized by the reaction devised by A. K. Bose wherein azidoacetyl chloride is reacted with a Schiff base to form the β-lactam. While in general a satisfactory technique, the azidoacetyl chloride reagent is relatively expensive and dangerous to work with in large quantities due to the risk of explosions.

Accordingly, particularly in view of the increasing research being directed to the preparation of biologically active β-lactams and the use of β-lactam intermediates in the synthesis of valuable antibacterial compounds such as the penicillins, cephalosporins, nocardicins, etc., there is need for a safe and inexpensive method for the preparation of β-lactams and related intermediates.

OBJECTS OF THE INVENTION

Accordingly, it is a general object of the present invention to provide a method for the production of both known and new azetidine carboxylic acids from inexpensive γ-lactone starting materials.

Another object of the present invention is to provide a method for the oxidative decarboxylation of azetidine carboxylic acids to directly form the corresponding β-lactams, as well as intermediates useful in such a method.

A further object of the present invention is to provide β-lactam derivatives which are useful as intermediates in the synthesis of biologically active lactams.

An additional object of the present invention is to provide a method for the total synthesis of pharmaceutically useful monocyclic β-lactams using inexpensive starting materials.

A more particular object of the present invention is to provide methods and intermediates for the synthesis of 3-aminonocardicinic acid and for the synthesis of nocardicins A and B therefrom.

Another specific object of the present invention is to provide methods and intermediates for the synthesis of the β-lactam-thiazolidine ring system common to all penicillins and the β-lactam-dihydrothiazine ring system common to all cephalosporins.

Upon study of the specification and appended claims, further objects and advantages of this invention will become apparent to those skilled in the art.

SUMMARY OF THE INVENTION

Briefly, the above and other objects, features and advantages of the present invention are attained in one aspect thereof by providing a process for preparing a cyclic lactam which comprises subjecting an amino carboxylic acid of the formula

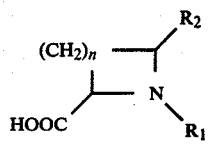

wherein $R_1$ is aliphatic or cycloaliphatic of up to ten carbon atoms, optionally interrupted by a sulfur or oxygen atom, and which is unsubstituted or substituted by alkoxy of 1–4 carbon atoms or by a group of the formula —NR'R" wherein R' and R" are each alkyl of 1–6 carbon atoms, aralkyl of 7 to 10 carbon atoms unsubstituted or substituted with hydroxy or alkoxy of 1–4 carbon atoms, aryl unsubstituted or substituted with hydroxy or alkoxy of 1 to 4 carbon atoms, or a heterocyclic ring of 4 to 7 members containing a total of 1–3 nitrogen, oxygen or sulfur hetero atoms or R' and R", together with the N-atom, collectively represent a heteromonocyclic ring of 4–7 members containing a total of 1–3 nitrogen, oxygen or sulfur hetero atoms which can be unsubstituted or substituted by an alkyl group of 1–4 carbon atoms; or $R_1$ is hydrocarbon aryl or aralkyl of 6–10 ring carbon atoms which is unsubstituted or substituted by alkyl of 1–4 carbon atoms, hydroxy, alkoxy of 1–4 carbon atoms, or by a group of the formula —NR'R" wherein R' and R" have the above-indicated values; or $R_1$ is a monovalent heterocyclic ring which is no more basic than imidazolyl and which contains 5–10 ring members and 1–3 nitrogen, oxygen or sulfur hetero atoms bonded to the —CH— group via a carbon-to-carbon single covalent bond;

$R_2$ is hydrogen or alkyl of 1–6 carbon atoms; and n is a positive integer of 1–10 inclusive to oxidative decarboxylation to form a corresponding cyclic lactam of the formula

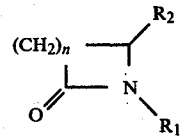

wherein $R_1$ and n have the above-indicated values.

In another aspect, the present invention provides novel dilithium salts of hydroperoxy acids formed by uptake of oxygen from an azetidine carboxylic acid dianion and a method for the conversion thereof into the corresponding β-lactam by oxidative decarboxylation.

In an additional aspect, the present invention provides a process for the preparation of azetidine carboxylic acids from a corresponding γ-lactone starting material using a pyridine cosolvent and substantially shorter reaction times than previously employed in the prior art to enhance the yields thereof.

In a further aspect, the present invention provides a method for the synthesis of biologically active β-lactams, particularly compounds related to the penicillins, cephalosporins, nocardicins and the like, and intermediate β-lactam products useful therein.

DETAILED DISCUSSION

In one aspect of the present invention, it has been found that α-carboxylic acid derivatives of cyclic amines of the general Formula I

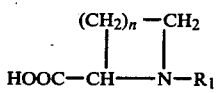

wherein $R_1$ is as defined hereinafter and n is a positive integer, preferably 1–10 and especially 1–3, can undergo oxidative decarboxylation by the oxygenation of dianions formed at low temperatures using an extremely strong base, such as lithium diisopropylamide (LDA).

While described principally with respect to the synthesis of β-lactams from γ-butyrolactone starting materials, it will be appreciated that this aspect of the present invention is equally applicable to the synthesis of corresponding γ- and δ-lactams from respectively larger lactone ring compounds, e.g., γ-lactams can be analogously prepared from δ-lactones, etc. A distinct advantage of the present process is the possibility of introducing a wide variety of substituents in the 1-position during the lactam formation process itself. By the appropriate selection of substituted lactone starting materials, additional substituents can be carried over into the lactam ring at the ω-position. The reaction sequence for this aspect of the present invention is set forth below.

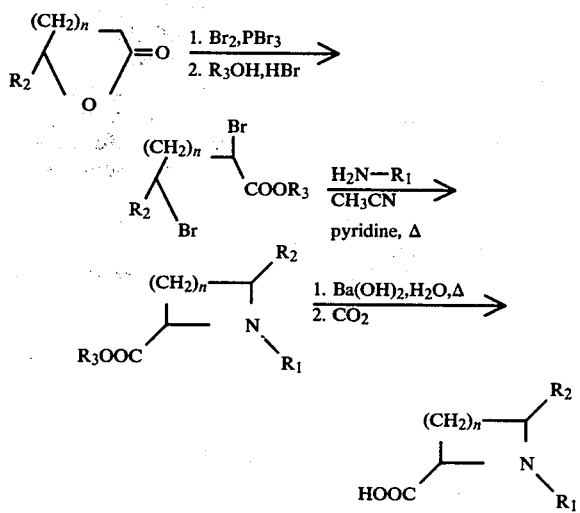

The lactone ring and dibromoester starting materials used in the above sequence are known in the art or can be prepared by methods analogous to those known in the art, e.g., see Cromwell et al, J. Hetero. Chem. 6:435 (1969).

$R_1$ in the above reaction scheme can be any organic radical having a carbon atom covalently bonded to the primary amino group $NH_2$, i.e., any primary amine residue which does not interfere with the subsequent oxidative decarboxylation step to form the desired β-lactam product. The only essential limitations are that $R_1$ lack an unmasked "active" hydrogen atom so as to be essentially non-reactive with the strong base under the reaction conditions employed and that it not sterically hinder the ring formation, although wide latitude appears possible in this latter connection. Preferably, $R_1$ is a group no more basic than imidazolyl. If desired, $R_1$ can be cleavable in a subsequent step, e.g., by hydrogenolysis or acidification, to form a hydrogen atom on the lactam nitrogen which can later be replaced by other groups.

$R_1$ values meeting the above criteria can be aliphatic, cycloaliphatic or aromatic and hydrocarbon or heteroatomic containing one or more nitrogen, oxygen or sulfur atoms.

Aliphatic or cycloaliphatic is preferably of up to 6 carbon atoms, e.g., alkyl, alkenyl, alkynyl, cycloalkyl or cycloalkenyl. Suitable alkyl groups include but are not limited to methyl, ethyl, n-propyl, isopropyl, n-butyl, isobutyl, sec.-butyl and tert.-butyl. Suitable alkenyl groups include but are not limited to vinyl, 2,2-dimethylvinyl, allyl, dimethylallyl, 1-propenyl, 1-butenyl, 2-butenyl, 3-methyl-2-butenyl, 1-pentenyl and 2-pentenyl. Suitable alkynyl groups include but are not limited to propynyl, butynyl and pentynyl. Suitable cycloalkyl groups include but are not limited to cyclopropyl, cyclobutyl, cyclopentyl and cyclohexyl optionally substituted, e.g., by alkyl or alkenyl of up to 4 carbon atoms to form cycloalkylalkyl or cycloalkylalkenyl, e.g., cyclopropylmethyl. Suitable cycloalkenyl groups include but are not limited to cyclobutenyl, cyclopentenyl and cyclohexenyl optionally substituted, e.g., by alkyl or alkenyl of up to 4 carbon atoms to form cycloalkenylalkyl or cycloalkenylalkenyl, e.g., cyclobutenylethyl.

Contemplated aliphatic or cycloaliphatic equivalents are such groups bearing one or more substituents, e.g., halogen atoms or lower alkoxy, e.g., methoxyethyl, chloromethyl, methoxybutyl and bromoethyl.

Aromatic is hydrocarbon aryl, preferably phenyl or naphthyl; hydrocarbon alkaryl, e.g., tolyl; or hydrocarbon aralkyl, preferably phenylalkyl or substituted phenalkyl of 1 to 4 carbon atoms in the alkyl substituent, e.g., benzyl or phenethyl. Suitable substituents of the phenyl or naphthyl group are lower alkyl groups, e.g., methyl; lower alkoxy groups, e.g., methoxy; halogen atoms, e.g., fluorine or chlorine. Suitable aromatic substituents include but are not limited to phenyl, o-, m- or p-tolyl, o-, m- or p-methoxyphenyl, o-, m- or p-fluorophenyl, o-, m- or p-chlorophenyl, α- or β-naphthyl. Aralkenyl is preferably phenylalkenyl of 2 to 6 carbon atoms in the alkenyl substituent, e.g., phenallyl.

$R_1$ can be a group of the formula $-(CH_2)_nR'R''$ or $NR'R''$ wherein n has the above-indicated values and wherein $R'$ and $R''$ are each alkyl of 1–6 carbon atoms, aralkyl of 7 to 10 carbon atoms unsubstituted or substituted with hydroxy or alkoxy of 1–4 carbon atoms, alicyclic aryl unsubstituted or substituted with hydroxy or alkoxy of 1 to 4 carbon atoms, or a heterocyclic ring of 4 to 7 members containing a total of 1–3 nitrogen, oxygen or sulfur hetero atoms, or $R'$ and $R''$ collectively form a heterocyclic ring which is no more basic than imidazolyl and which contains 5–10 ring members and 1–3 nitrogen, oxygen or sulfur atoms, each of said members being unsubstituted or monosubstituted by alkyl of 1–4 carbon atoms.

Monovalent heterocyclic ring substituents encompassed by the present invention are generally of 5-10, preferably 5 or 6 ring atoms of which 1-4, generally 1-3 and preferably 1 or 2, are oxygen, nitrogen and/or sulfur heteroatoms. The heterocyclic ring can be non-hydrogenated, e.g., imidazolyl, oxazolyl, thiazolyl, etc.; partially hydrogenated, e.g., imidazolinyl, oxazolinyl, thiazolinyl, etc.; or completely hydrogenated, e.g., piperazinyl, morpholino, tetrahydropyrimidinyl, etc.

Suitable heterocyclic groups can be those derived from a five member heterocyclic ring containing a single heteroatom, e.g., furyl, thienyl or pyrrolyl; a five member heterocyclic ring containing two heteroatoms, e.g., pyrazolyl, imidazolyl, oxazolyl, oxazolinyl, isoxazolyl, isoxazolinyl, thiazolyl or thiazolinyl; a five member heterocyclic ring containing 3 heteroatoms, e.g., triazolyl, oxadiazolyl, thiadiazolyl, dioxazolyl and oxathiazolyl; or a five member heterocyclic ring containing 4 heteroatoms, e.g., tetrazolyl, oxatriazolyl and thiatriazolyl. Preferred heterocyclic groups derived from a five member heterocyclic ring are furyl, thienyl, pyrrolyl, pyrazolyl, imidazolyl, isoxazolyl and thiazolyl, especially thienyl.

Suitable heterocyclic groups can also be those derived from a six member heterocyclic ring containing a single heteroatom, e.g., pyridyl, pyranyl and thiopyranyl, preferably pyridyl; a six member heterocyclic ring containing two ring heteroatoms, e.g., dioxinyl, pyridazinyl, pyrimidinyl, pyrazinyl, piperazinyl, oxazinyl and morpholino; or groups derived from a six member heterocyclic ring containing 3 ring heteroatoms, e.g., triazinyl, oxathiazinyl and oxadiazinyl. Preferred heterocyclic groups derived from a six member heterocyclic ring are pyridyl, pyridazinyl, pyrimidinyl, piperazinyl or morpholino.

Preferred heterocyclic ring values for $R_1$ are furyl, thienyl, pyrrolyl, oxazolyl, imidazolyl and indolyl.

$R_2$ in the above formulae is preferably hydrogen but can also be lower alkyl of 1-6, preferably 1-3, carbon atoms.

$R_3$ can be any hydrolyzable ester residue, the particular nature thereof being unimportant with respect to the desired product since the intermediate ester is hydrolyzed prior to oxidative decarboxylation to split off the $R_3$ group.

Suitable ester residues $R_3$ meeting the above criteria can be aliphatic, cycloaliphatic or aromatic and hydrocarbon or heteroatomic containing one or more nitrogen, oxygen or sulfur atoms as defined above; preferably, $R_3$ is alkyl of 1-6 carbon atoms.

Various methods for the preparation of some azetidine carboxylic acids have been described in the literature, e.g., by Cromwell et al, in J. Hetero. Chem. 6:435(1969). However, under the conditions employed ($CH_3CN$, reflux, 24 hours) for formation of the esters, it has been found that these reactions are not of a general nature. That is to say, in many cases when amines other than those specifically employed in the aforementioned technique were used, little or no desired azetidine carboxylic ester product was obtained. Accordingly, alternative reaction conditions had to be developed to permit introduction of various types of amines in the above reaction scheme. It has now been found that the use of an organic base, e.g., pyridine, as a cosolvent with $CH_3CN$ in volume ratios of 10:1-1:1, preferably about 5:3, in conjunction with substantially shorter reaction times, e.g., of preferably less than 6 hours, results in significantly improved yields of azetidine carboxylic acids from inexpensive and readily available γ-lactones.

The use of a cosolvent in accordance with the present invention results in a dramatic improvement in yields. The only requirements of the cosolvent are that it must be basic but non-nucleophilic and hence inert with respect to the reactants and desired product formed. Cosolvents include but are not limited to triethylamine and pyridine, either of which in conjunction with $CH_3CN$ and used in a ratio of about 5:3 $CH_3CN$: cosolvent(v-v) gave the desired products in yields of 50-70%. Other polar solvents, including but not limited to THF, DMSO, etc., may be substituted for $CH_3CN$ accordingly.

In the above reaction scheme, it is possible to employ varying reaction temperatures. At ambient pressures, temperatures ranging from 0° C. to the boiling point of the lowest boiling component of the solvent system employed can be used. The preferred temperature range is 20°-60° C. at atmospheric pressure, and the reaction proceeds well at ambient temperatures. However, higher or lower temperatures can be employed depending upon the pressure at which the reaction is conducted.

While reaction time in accordance with the above scheme are substantially shorter than those heretofore employed, they also can be varied depending upon the reaction temperature and pressure utilized. Typically, yields after recovery and distillation of a reaction mixture run for 6 hours at 60° C. readily reached 60%, based on the starting materials employed.

Hydrolysis of the azetidine ester can be effected by any strong inorganic hydroxide, e.g., alkali metal hydroxides, alkaline earth metal hydroxides, etc.; preferably, hydroxides which form water-insoluble precipitates are employed, e.g., barium hydroxide. In this manner, the azetidine ester is readily hydrolyzed by refluxing in aqueous media followed by neutralization, e.g., with excess $CO_2$, to yield the desired azetidine carboxylic acid which can be isolated by filtration of the inorganic carbonate precipitate, removal of residual water followed by dissolution in chloroform and removal of residual solvent.

The azetidine carboxylic acids are valuable starting materials which can be subjected to oxidative decarboxylation to form a corresponding cyclic lactam. For example, oxidative decarboxylation can be effected by forming a dianion of a hydroperoxy acid, e.g., a dilithium salt of the formula

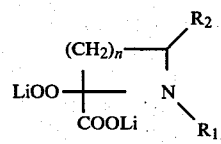

wherein n, $R_1$ and $R_2$ have the above-indicated values which, upon acidification, readily converts into the corresponding cyclic lactam. An alternative example of another suitable oxidative decarboxylation technique is described by Trost et al in JACS97:3528 (1975).

The conversion of the azetidine carboxylic acids to the corresponding β-lactams can be effected under a wide variety of reaction conditions. However, it is essential that a polar, aprotic solvent or solvent mixture be employed in order to effect dissolution of the intermediate dianion species. Typical such solvents are well known in the art and include THF, HMPA, diethyl ether, etc., either alone or in combination.

Aside from the use of a suitable solvent, the formation of the dianion intermediate requires specific precautionary measures known to those skilled in the art. The reaction must be conducted in an inert atmosphere, e.g., nitrogen, argon, neon, helium, etc., preferably nitrogen or argon, and the inert atmosphere should be maintained at all times. Equipment should be scrupulously dried by heating prior to use so as to remove moisture to below tolerable levels. Choice of the strong base employed to form the dianion must be such that the compound chosen is sufficiently basic with respect to the proton to be abstracted as well as being non-nucleophilic. Generally, bases in which the corresponding conjugate acid has a pKa equal to or greater than 19, preferably greater than 26, are suitable for proton abstraction from a large number of azetidine carboxylic acids. Such bases include but are not limited to $KO-C(CH_3)_3$,

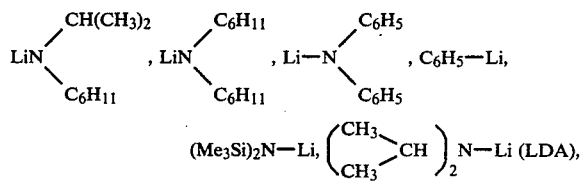

etc., with the use of the latter preferred.

The subsequent reaction of the thus-formed dianions with dry molecular oxygen can be effected by simply bubbling gaseous oxygen through the reaction solution. Inverse addition is preferred, wherein the solution of dianion is added to dry oxygen-saturated solvent, e.g., diethyl ether at $-78°$ C., to form the intermediate hydroperoxy acid. These intermediates are not usually isolated, but qualitatively confirmed, e.g., by the use of KI-starch paper. The hydroperoxy acid salts can, if desired, be isolated by simple removal of volatile materials in vacuo immediately subsequent to the oxidation step.*

*In cases where other acidic protons on the carbon adjacent to nitrogen (in the primary amine component) may be involved in dianion formation, it has been found necessary to utilize an extra equivalent of base prior to oxygenation, presumably in order to form the trianion. (See Example 8).

The formation of the $\beta$-lactam via decomposition of the hydroperoxy acid salts is effected by treatment with an acid solution which is sufficiently strong to fully neutralize the dianions. As it is difficult in practice to ascertain the actual percent conversion in the previous steps of the reaction scheme, this is generally determined empirically in each case. The use of excess acid results in reduced yields of the desired $\beta$-lactam product, so that it is important in assuring a good yield that no more acid be employed than theoretically required to neutralize the equivalents of strong base added previously to form the dianion.

The $\beta$-lactam product can then be isolated and purified by conventional techniques, which will be chosen depending on the particular molecular structure and state of matter obtained. Solids or liquids can both be chromatographed on florisil or alumina, e.g., using chloroform-ether as an eluent; liquids can be kugelrohr distilled under high vacuum.

It will be appreciated that the process of the present invention provides a simple manner for preparing $\beta$-lactams bearing a wide variety of substituents on the lactam nitrogen atom. In this connection, the reactant $R_1-NH_2$ preferably is straight-chain or branched alkyl, e.g., methyl, ethyl, n-propyl, isopropyl, n-butyl, isobutyl, sec.-butyl, tert.-butyl, n-pentyl, isoamyl, n-hexyl, n-heptyl, n-octyl, 2-ethylhexyl, n-nonyl, n-decyl, n-undecyl, n-dodecyl, n-tridecyl, n-tetradecyl; alkenyl, e.g., allyl, crotyl; alkynyl, e.g., masked propargyl; hydroxyalkyl wherein the hydroxy group is masked and separated by at least 2 carbon atoms from the amine group, e.g., masked 2-hydroxyethyl, 2-hydroxypropyl, 3-hydroxypropyl; alkoxyalkyl, e.g., 2-methoxyethyl, 2-ethoxyethyl, and the corresponding groups having an oxygen or sulfur atom in the chain; tertiary aminoalkyl, e.g., wherein the amino group is separated by at least 2 carbon atoms from the primary amine group, including N,N-dialkylaminoalkyl; cycloalkyl and cycloalkyl-alkyl primary amines, e.g., containing 3-8 ring carbon atoms, preferably 5 or 6, e.g., cyclopentyl, cyclohexyl, 2-cyclohexylethyl, 3-cyclohexylpropyl; azacycloalkyl, azacycloalkylalkyl and related cyclic groups, preferably containing a total of 5-6 ring members and 1-2 of N and 0-1 of O or S as ring members in addition to ring carbon atoms and wherein the ring is at least 1 carbon removed from the amino group, e.g., by a lower alkylene. In principle, the oxidative decarboxylation can be also performed on primary amines of the above formula having a free hydroxyl group, but practical considerations require masking of the hydroxyl group for the reasons that the proton thereof is acidic and thus another equivalent of base (e.g., LDA) would be required; the resultant trianionic species would have different solubility properties than the dianion, so that a different solvent system might be required; and additional acid would be required in the final decarboxylation step. Suitable hydroxyl protecting or masking groups are well known in the art and include but are not limited to benzyl, methyl, trialiphatic silyl, THP, THF, EVE (from ethyl vinyl ether), etc. Insertion and removal of these groups employs conventional techniques which are well documented in the literature.

Especially preferred as intermediates for subsequent synthesis of $\beta$-lactam containing compounds having pharmaceutical utility are those wherein the lactam nitrogen is substituted with an alkylene dialkoxy group of any desired chain length, preferably lower alkylene di-lower alkoxy of 1-8 carbon atoms in the alkyl group and 1-4 carbon atoms in each alkoxy group, e.g., ethylenedimethoxy. An additional preferred class of $\beta$-lactams obtainable in accordance with the present invention is those wherein the lactam nitrogen is substituted by an alkenyl group of any desired chain length, preferably of 3-10 carbon atoms in which the ethylenic unsaturation is spaced by at least one carbon atom from the lactam nitrogen, e.g., allyl. As with the acid labile acetal, these alkenyl-substituted $\beta$-lactams have latent functionality and facilitate expansion of the side chains to form a variety of end products.

Suitable alkenyl-substituted $\beta$-lactams are formed from primary amine reactants $H_2NR_1$ of the general formula:

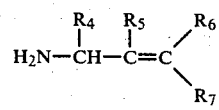

wherein R$_4$ is aliphatic, cycloaliphatic or aromatic and hydrocarbon or heteroatomic as defined hereinabove for R$_1$, especially as in nocardicin; and R$_5$, R$_6$ and R$_7$ are each hydrogen or alkyl of 1-10, preferably 1-3, carbon atoms.

Suitable acetals are formed from primary amine reactants H$_2$NR$_1$ of the general formula:

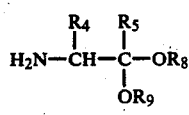

wherein R$_4$ and R$_5$ have the above-indicated values and R$_8$ and R$_9$ are each alkyl of 1-6 carbon atoms or together form alkylenedioxy.

Alkylenedioxy is preferably of 2-4 carbon atoms, e.g., ethylenedioxy, propylenedioxy, etc.

As previously indicated, the lactam nitrogen atom can be substituted either prior or subsequent to formation of the lactam ring. As 6 and 7-membered rings, e.g., N-methylproline, are easily subjected to oxidative decarboxylation in accordance with the present invention, use of the appropriate starting materials bearing the desired substituent on the lactam nitrogen is now possible with a large variety of substituents. The only requirement is that the primary amine employed must be sufficiently basic to displace the bromine atoms in the azetidine forming reaction, i.e., either sufficiently basic in the free form or in the form of a strongly basic salt, such as can be formed by reaction of the amine with sodium hydride, n-butyl lithium, etc. The use of a strongly basic salt is generally required with primary amines in which the amine carbon atom is attached to a ring structure, which is aromatic or ethylenically unsaturated. In particular, and presently preferred are such amines wherein the R$_1$ group contains a thioether, ether, olefin, or acetal masking an aldehyde or ketone. Hydroxyl groups must be masked, e.g., by etherification, and carboxyl groups are preferably masked, e.g., by esterification, when located near the amine nitrogen atom.

Substitution of the β-lactam at the 3-position is readily accomplished according to techniques well known in the literature, e.g., see Kuhlein and Jensen, Liebigs. Ann. Chem. 1974, pp. 369-402.

As with the details of the oxidative decarboxylation technique, this can be achieved with a variety of reaction conditions. Preferred substituents at the 4-position of the lactam ring can be produced during ring formation; presently preferred are those substituents occuring at this position in the known active monocyclic β-lactams, e.g., p-methoxyphenyl, o-nitrophenyl, o-aminophenyl, 1-(amidobenzyl)phenyl, 2-furanyl, p-carboxyphenyl and the like. Similarly, preferred substitutents on the lactam nitrogen are those commonly occuring in antibacterially active monocyclic β-lactams, e.g., p-acetylphenyl, diphenylmethylene, phenyl, p-methoxyphenyl, p-carboxyphenyl, p-carboxymethylphenyl and benzyl. Preferred substituents at the 3-position are the azide group N$_3$ which is readily reduced to the amino group NH$_2$, which in turn can be converted into a corresponding amide by suitable reaction with acid residues found in the penicillins and cephalosporins, e.g., phenylacetyl, phenoxyacetyl, 2-pentenoyl, n-pentanoyl, n-heptanoyl, p-hydroxyphenylacetyl, allythioacetyl, etc.

Compounds of this invention which contain a center of asymmetry ordinarily are obtained in the racemic form. The racemates can be separated into their optical antipodes in accordance with a plurality of known methods described in the literature; chemical separation is preferred. According to this procedure, diastereomers are formed from the racemic mixture by reaction with an optically active auxiliary agent. Thus, an optically active base can be reacted with the carboxyl group, or an optically active acid with the amino group, of a compound of this invention. For example, diastereomeric salts of compounds containing a free carboxyl group can be formed with optically active amines, e.g., quinine, cinchonidine, brucine, cinchonine, hydroxyhydrindamine, morphine, 1-phenylethylamine, 1-naphthylethylamine, phenyloxynaphthylmethylamine, quinidine and strychnine, basic amino acids, e.g., lysine, arginine and amino acid esters; or diastereomeric salts of basic compounds can be formed with optically active acids, e.g., (+)- and (−)-tartaric acid, dibenzoyl-(+)- and -(−)-tartaric acid, diacetyl-(+)- and -(−)-tartaric acid, camphoric acid, β-camphorsulfonic acid, (+)-and (−)-mandelic acid, (+)- and (−)-malic acid, (+)- and (−)-2-phenylbutyric acid, (+)- and (−)-dinitrodiphenic acid, or (+)- and (−)-lactic acid. In a similar manner, esterdistereomers can be produced by the esterification of compounds containing a free carboxyl group with optically active alcohols, e.g., borneol, menthol or 2-octanol. The thus-obtained mixtures of diastereomeric salts and/or esters can be separated by selective crystallization. The desired optically active compounds can be produced by hydrolytic separation of the isolated diastereomeric compound.

A presently preferred aspect of the present invention relates to the synthesis of 3-aminonocardicinic acid (3-ANA), useful as an intermediate in the synthesis of nocardicin. 3-ANA can be obtained using the method of the present invention in the following reaction sequence:

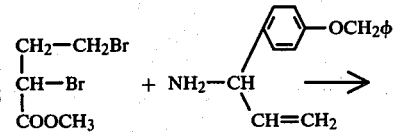

(1)

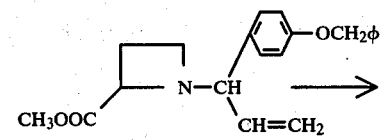

(2)

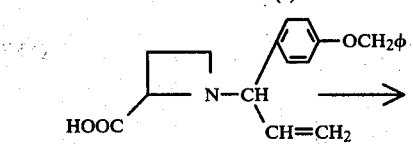

(3)

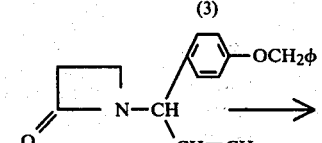

(4)

-continued

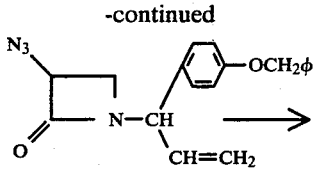
(5)

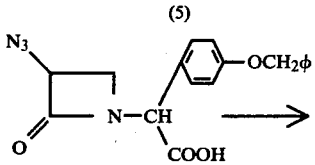
(6)

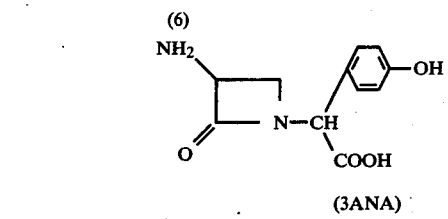
(3ANA)

Especially preferred compounds of the present invention are those of the above formulae in which one or more of the substituents thereon have the following values:

(a) $R_1$ is alkyl or alkenyl of up to 6 carbon atoms which is unsubstituted or substituted as aforesaid and which is optionally interrupted by a sulfur atom;

(b) $R_1$ is alkyl or aryl, preferably hydrocarbon aryl, substituted by —NR'R";

(c) $R_1$ is alkenyl of the formula

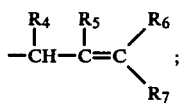

(d) $R_1$ is alkenyl of the formula

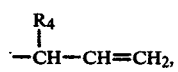

especially wherein $R_4$ is p-alkoxyphenyl or p-benzyloxyphenyl;

(e) $R_1$ is an acetal group of the formula

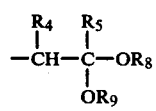

(f) $R_1$ is as in (e), wherein $R_4$ is p-alkoxyphenyl or p-benzyloxyphenyl;

(g) $R_2$ is hydrogen or alkyl of 1-3 carbon atoms, especially hydrogen;

(h) $R_3$ is alkyl of 1-4 carbon atoms, benzyl or benzhydryl;

(i) $R_4$ is alkoxy, aryloxy, alkoxyaryl or aryloxyaryl;

(j) $R_4$ is p-alkoxyphenyl or p-benzyloxyphenyl;

(k) $R_5$ is hydrogen or alkyl of 1-3 carbon atoms, especially hydrogen;

(l) $R_6$ and $R_7$ are each hydrogen or alkyl of 1-3 carbon atoms, especially hydrogen;

(m) $R_8$ and $R_9$ are each alkyl of 1-3 carbon atoms, especially methyl or ethyl, or $R_8$ and $R_9$ together form alkylenedioxy of 2-3 carbon atoms;

(n) azetidine carboxylic acid azides of the formula

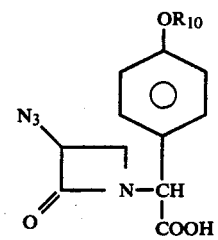

wherein $R_{10}$ is a cleavable hydroxyl masking group, preferably alkyl, alkanoyl, aroyl, arylmethyl, alkylsulfonyl, arylsulfonyl or trialkylsilyl and especially methyl, benzyl or benzhydryl;

(o) β-lactam azides of the formula

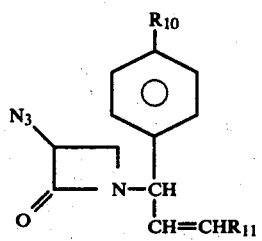

wherein $R_{10}$ is as defined in (n) and $R_{11}$ is hydrogen or alkyl of 1-6 carbon atoms, especially hydrogen.

(p) $R_1$ contains a heterocyclic ring as defined herein which is separated from the nitrogen atom to which $R_1$ is bonded by at least one carbon atom, e.g., by alkylene of 1-10, preferably 1-6, carbon atoms such as methylene, ethylene, n-propylene, etc., especially methylene;

(q) $R_1$ contains a hydrocarbon aryl or aralkyl ring as defined herein which is separated from the nitrogen atom to which $R_1$ is bonded by at least one carbon atom, e.g., by alkylene of 1-10, preferably 1-6, carbon atoms such as, methylene, ethylene, n-propylene, etc., especially methylene. Particularly preferred such values for $R_1$ are benzyl or benzhydryl, either unsubstituted or substituted as defined herein.

Specific compounds of the present invention, in addition to those shown above and in the following examples, include but are not limited to the following:

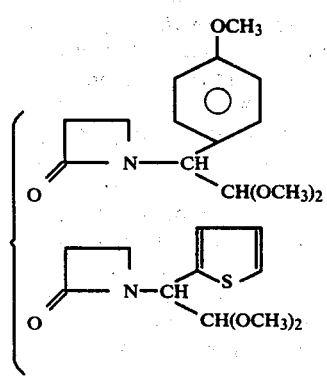

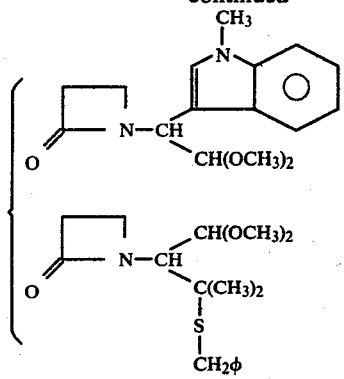

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight. The values obtained in elemental analyses are within commonly accepted limits of error. All new products gave the expected parent peaks in the mass spectra and the expected absorption peaks in NMR and IR.

EXAMPLE 1

Preparation of N-t-butyl-2-Azetidinone

To a solution of lithium diisopropylamide (LDA) in THF at 0° under $N_2$ was added 0.47 g (3 m moles) of (1) all at once. After stirring at 0° for 1 hour, the solution was cooled to −78° and added via syringe to a reaction well which contained oxygen-saturated $Et_2O$ at −78° being continuously circulated and dried. After five minutes, 1.4 g (2.3 equiv.) of p-toluenesulfonic acid monohydrate, dissolved in 10 ml of dry THF, was added to the reaction mixture. The cooling bath was then removed and the well allowed to reach ambient temperature. The mixture was filtered, dried over $MgSO_4$ and concentrated in vacuo. Trituration with $Et_2O$ followed by filtration and removal of solvent gave an oil which was chromatographed on alumina ($CHCl_3$-$Et_2O$) to afford 225 mg (60%) of the title compound (2); b. p. (bath) 75° at 3.6 mm Hg; ir 1740 cm$^{-1}$; nmr δ 3.18 (t, 2H), 2.77 (t, 2H), 1.33 (s, 9H). Comparison with spectral data of an authentic sample prepared earlier in these laboratories served further to confirm the identity of the product.

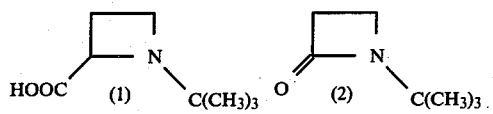

EXAMPLE 2

Preparation of N-n-pentyl-2-Azetidinone

The oxidative decarboxylation was performed on 0.51 g (3 m moles) of amino acid (1) in the same fashion as that described in Example 1. Employment of the same workup and isolation procedures afforded 260 mg (61%) of the title compound (2); b. p. (bath) 90° at 0.2 mm Hg; ir 1745 cm$^{-1}$, nmr δ 3.13 (m, 4H), 2.84 (t, 2H), 1.32 (m, 6H), 0.88 (t, 3H); mass spec. M+ 141; elemental analysis: Calc ($C_8H_{15}NO$) C: 68.04, H: 10.71, N: 9.92; Found C: 67.87, H: 10.68, N: 9.87.

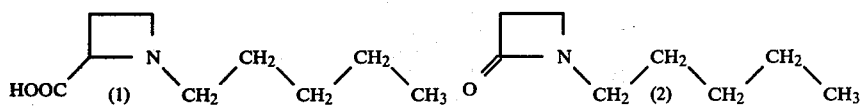

EXAMPLE 3

Preparation of N-(2-phenethyl)-2-Azetidinone

The oxidative decarboxylation was performed on 0.62 g (3 m moles) of amino acid (1) in the same fashion as that described in Example 1. Employment of the same workup and isolation procedures afforded 261 mg (50%) of the title compound (2); b. p. (bath) 120° at 0.17 mm Hg; ir 1745 cm$^{-1}$; nmr δ 7.27 (m, 5H), 3.44 (t, 2H), 3.04 (t, 2H), 2.82 (m, 4H); mass spec M+ 175; elemental analysis: Calc ($C_{11}H_{13}NO$) C: 75.40, H: 7.48, N : 7.99; Found C: 75.44, H: 7.63, N: 8.17.

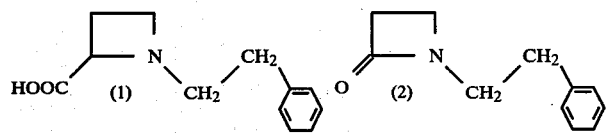

EXAMPLE 4

Preparation of N-cyclohexyl-2-Azetidinone

The oxidative decarboxylation was performed on 0.55 g (3 m moles) of amino acid (1) in the same fashion as that described in Example 1. Employment of the same workup and isolation procedures afforded 230 mg (50%) of the title compound (2); b. p. (bath) 120° at 1 mm Hg; ir 1740 cm$^{-1}$; nmr δ 3.43 (s, br, 1H), 3.21 (t, 2H), 2.83 (t, 2H), 1.50 (m, 10H). Comparison with spectral data of an authentic sample prepared earlier in these laboratories served further to confirm the identity of the product.

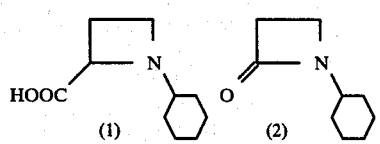

EXAMPLE 5

Preparation of N-cyclooctyl-2-Azetidinone

The oxidative decarboxylation was performed on 0.63 g (3 m moles) of amino acid (1) in the same fashion as that described in Example 1. Employment of the same workup and isolation procedures afforded 282 mg (52%) of the title compound (2); b. p. (bath) 105° at 0.15 mm Hg; ir 1740 cm$^{-1}$; nmr $\delta$ 3.75 (s, br, 1H), 3.19 (t, 2H), 2.80 (t, 2H), 1.65 (m, 14H); mass spec. M$^+$181; elemental analysis: Calc (C$_{11}$H$_{19}$NO) C: 72.88, H: 10.56, N: 7.73; Found C: 73.08, H: 10.49, N: 7.60.

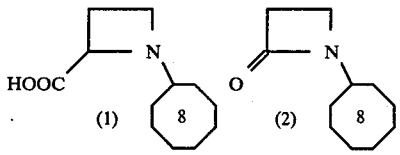

EXAMPLE 6

Preparation of N-(2,2-dimethoxyethyl)-2-Azetidinone

The oxidative decarboxylation was performed on 0.92 g (5 m moles) of the amino acid (1) in the same fashion as that described in Example 1. Employment of the same workup and isolation procedures afforded 400 mg (50%) of the title compound (2); b. p. (bath) 75° at 0.23 mm Hg; ir 1742 cm$^{-1}$; nmr $\delta$ 4.47 (t, 1H), 3.38 (s, 6H), 3.36 (t, 2H), 3.33 (d, 2H), 2.95 (t, 2H); mass spec. M$^+$159; elemental analysis: Calc (C$_7$H$_{14}$NO$_3$) C: 52.82, H: 8.23, N: 8.80; Found C: 52.92, H: 8.15, N: 8.87.

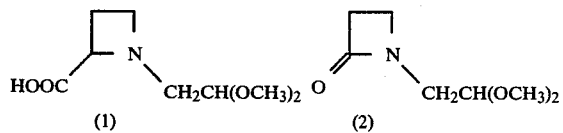

EXAMPLE 7

Preparation of $\beta$-lactams II, III and IV from I

The conversion of $\beta$-lactams to acylamino derivatives was carried out as described below. This procedure follows the published report "Substitutionsreaktionen an Cephamderivaten." by K. Kuhlein and H. Jensen in Liebigs Ann. Chem., 369–402 (1974) and readily yields derivatives at the 3-position corresponding to the acylamino side chain in penicillin. The reaction sequence is as follows:

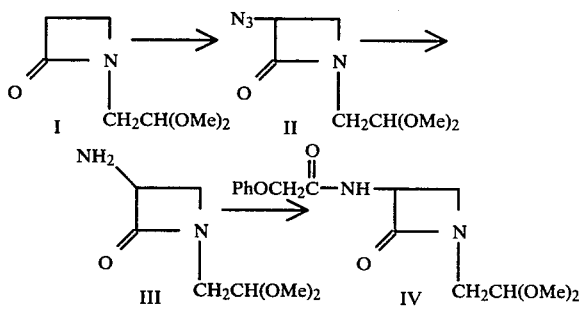

(A) Introduction of the 3-Azide Group 0.92 g. (5 mmole) of $\beta$-lactam (I) was added dropwise in THF to a solution of lithium diisopropylamide (1.2 equivalents) [obtained from 0.71 g (7 mmole) of diisopropylamine and 3.8 ml. (6 mmole) of n-butyllithium] in THF at −78° under a nitrogen atmosphere. The mixture was allowed to stir for seven hours to form the anion. p-Toluenesulfonyl azide, 1.2 g. or 6 mmole, (1.2 equivalents) in 7 ml. diethyl ether was added dropwise, and stirring at −78° C. was continued for one hour after the addition was complete. Trimethylchlorosilane 1.6 g. (14.4 mmole) (2.4 equivalents) in 5 ml. ether was added dropwise, and the solution was allowed to warm to room temperature over two hours. The mixture was then brought to reflux and heating was continued for ten hours. The reaction mixture was filtered and concentrated under aspirator vacuum. The resultant oil was mixed with water and carefully neutralized with sodium bicarbonate. The mixture was extracted into excess methylene chloride, dried over magnesium sulfate, filtered and again concentrated in vacuo. The resultant oil (0.5 g.) was purified by chromatography (silica gel, chloroform) to yield the liquid 3-azido $\beta$-lactam (II) (50%): ir 2950, 2840, 2803, 1760, 1407, 1320, 1260, 1195, 1120, 1070, 980, 920 and 820 cm$^{-1}$; nmr $\delta$ 4.60 (doublet of doublets, J=4.5 and 1 cps, 1H), 4.55 (triplet, J=4.5 cps, 1H), 3.75.–3.35 (multiplets, from which emerges at $\delta$ 3.40 a strong sharp singlet, 10H).

(B) Reduction to the 3-Amino Derivative (III)

The amine (III) was prepared by mild catalytic hydrogenation of compound II. Compound II 81 mg. (0.36 mmole) was reduced at 38 psi H$_2$ in 100 ml. methyl acetate over 150 mg. Adam's PtO$_2$ catalyst in a Parr apparatus. The hydrogenation was complete after 3 hours. Filtration and concentration of the reaction mixture gave 57 mg. of liquid amine (III) (90%); ir 3380, 3300, 2960, 2840, 1745, 1410, 1295, 1250, 1200, 1135, 1070, 980, 920, and 820 cm$^{-1}$; nmr $\delta$ 4.5 (triplet, J=4.5 cps, 1H), 4.2 (multiplet, 1H), 3.7–3.2 (multiplets, from which emerges at $\delta$ 3.4 a strong sharp singlet).

(C) Amidation to form the Phenoxyacetylamino Derivative (IV)

The 57 mg. (0.33 mmole) amine obtained in the previous reaction was mixed with 33 mg. (1 equivalent) of triethylamine in 15 ml. chloroform, to which was added dropwise 0.06 g. (1 equivalent) phenoxyacetyl chloride in 3 ml. of chloroform. The mixture was stirred for one hour at room temperature and then poured into an excess of saturated aqueous sodium bicarbonate solution. The organic portion was drawn off, and the aqueous layer was back-extracted with further portions of chloroform. The combined chloroform layers were dried over anhydrous magnesium sulfate, filtered and concentrated to give 100 mg. (0.33 mmole) of Compound IV as a stable crystalline solid m.p. 74.5–75.5 (100%); ir 3300, 2950, 2840, 1755, 1685, 1600, 1520, 1500, 1450, 1300, 1230, 1180, 1130, 1080, 760, and 700 cm$^{-1}$; nmr $\delta$ 7.3–6.9 (multiplets, 5H), 5.05 (multiplet, 1H), 4.5 (coincident triplet J=4.5 cps) and singlet, 3H), 3.7 (triplet J=4.5 cps, 1H) and 3.4 (multiplets, 8H).

EXAMPLE 8

Preparation of N-benzyl-2-Azetidinone

To a solution of LDA (6.3 mmoles) in THF at 0° under $N_2$ was added 0.38 g (2 mmoles) of compound (1) all at once. After stirring at 0° for one hour, the solution was cooled to −78° and one equivalent (ca 45 ml) of oxygen, stored in a gas buret was introduced under the surface of the solution. After 15 minutes, 1.2 g (6.3 mmoles) of p-toluene sulfonic acid monohydrate dissolved in 15 ml THF was added. Workup as described above afforded 0.16 g (50%) of the title compound (2); b.p. 55° at 0.05 mm Hg; ir 1730 cm−1; NMR, δ 7.30 (s,5H), 4.36 (s,2h), 3.17 (t,2h), 2.98 (t,2h).

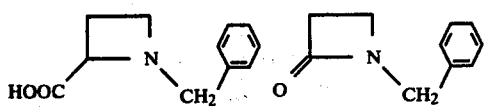

EXAMPLE 9

Preparation of Nocardicin

The oxidative decarboxylation procedure provides a novel route to the monocyclic β-lactams related to nocardicin. Illustrative procedures which can be used to form 3-amino nocardicinic acid (3-ANA) are outlined below.

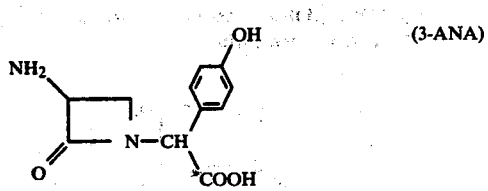
(3-ANA)

Method A

This involves the use of substituted allylamines which can be condensed with a 1,3-dibromoester to yield the N-substituted 2-carbomethoxyazetidine. Hydrolysis thereof to the acid is followed by oxidative decarboxylation in accordance with the present invention to form the β-lactam.

Introduction of the azido group at the 3-position thereof, e.g., by treatment of the anion at low temperature with tosyl azide, yields (6) which is then oxidized (osmium tetroxide or $RuO_4$, periodate) to yield the acid azide. Mild catalytic reduction thereof by $H_2$ yields 3-ANA.

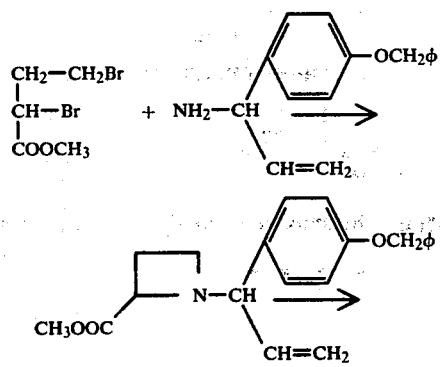

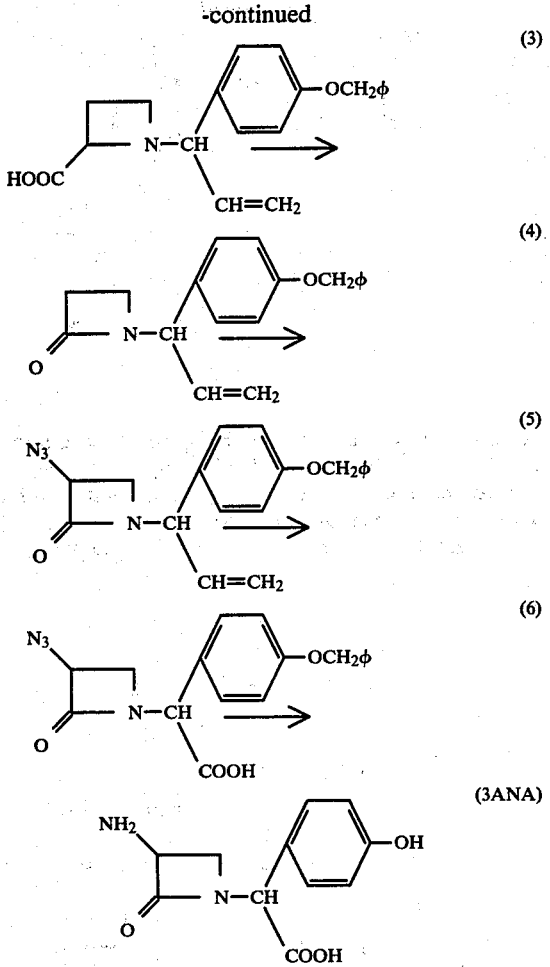

Method B

Reaction of benzylamine with the dibromoester gives the N-substituted azetidine 2-carboxylic ester; hydrolysis followed by oxidative decarboxylation yields the lactam (see Example 8). Introduction of the 3-azido group in the usual way is followed by hydrogenation to yield the 3-amino lactam. Acetylation of the 3-amino group is followed by alkylation of the lactam nitrogen, e.g., see the method of N. H. Cromwell and R. M. Rodebaugh, J. Heterocyclic Chem., 6:439 (1969), using sodium hydride or thallium ethoxide and the bromoester in a manner recently reported by Japanese workers in Belgium Pat. No. 830,934.

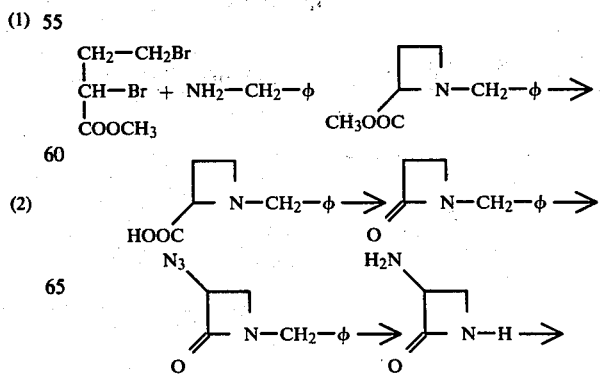

-continued

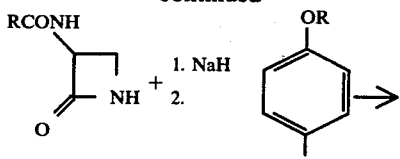

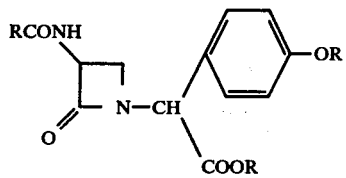

An alternate route to the acylated 3-aminoazetidinone involves the N-allylazetidinone; reaction with N-bromosuccinimide yields the bromo derivative which, with cold aqueous bicarbonate, forms the 3-aminoazetidinone via the unstable carbinolamine.

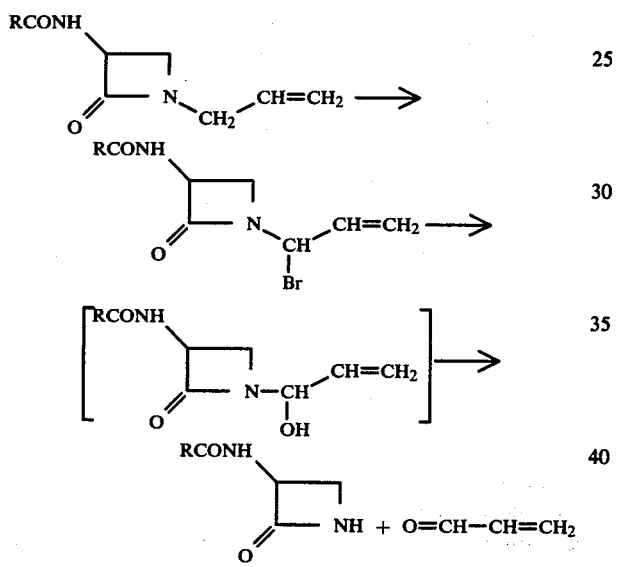

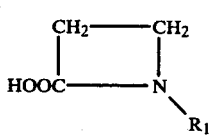

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for preparing a lactam from an aminocarboxylic acid of the formula

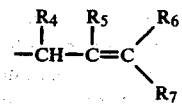

where $R_1$ is selected from the group consisting of:
(a) an alkenyl group of the formula

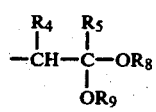

wherein $R_4$ is phenyl, phenylalkyl of 1–4 carbon atoms in the alkyl group or phenylalkenyl of 2–4 carbon atoms in the alkenyl group, each of which is unsubstituted or monosubstituted by lower alkyl, lower alkoxy or halogen; and $R_5$, $R_6$ and $R_7$ are hydrogen or alkyl of 1–3 carbon atoms; and
(b) an acetal of the formula

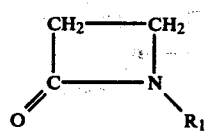

wherein $R_4$ and $R_5$ have the above-indicated values while $R_8$ and $R_9$ are each alkyl of 1–6 carbon atoms or together form ethylenedioxy or propylenedioxy; which comprises oxygenation of a dianion formed at low temperatures by reacting said aminocarboxylic acid with a non-nucleophilic base whose corresponding conjugate acid has a pKa equal to or greater than 19 in a polar, aprotic solvent to form a corresponding dianion intermediate and acidification of said intermediate to form a corresponding lactam of the formula $$\begin{array}{c} CH_2\text{———}CH_2 \\ | \quad\quad\quad | \\ C\text{———}N \\ \parallel \quad\quad\quad | \\ O \quad\quad\quad R_1 \end{array}$$

wherein $R_1$ has the above-indicated values.

2. A process according to claim 1, wherein $R_1$ is said alkenyl group.

3. A process according to claim 2, wherein $R_5$, $R_6$ and $R_7$ are each hydrogen.

4. A process according to claim 3, where $R_4$ is p-alkoxyphenyl or p-benzyloxyphenyl.

5. A process according to claim 1, wherein $R_1$ is an acetal group.

6. A process according to claim 5, wherein $R_4$ is p-alkoxyphenyl or p-benzyloxyphenyl.

7. A process according to claim 1, wherein said oxidative decarboxylation includes acidifying a dilithium salt of a hydroperoxy acid of the formula:

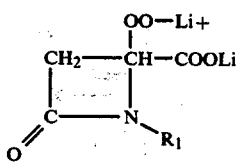

wherein $R_1$ has the above-indicated values to form said lactam.

* * * * *